US006749429B1

(12) United States Patent
Haraden et al.

(10) Patent No.: US 6,749,429 B1
(45) Date of Patent: Jun. 15, 2004

(54) MATRIX BAND FOR USE IN DENTISTRY

(76) Inventors: William J. Haraden, 1860 Countryside Dr., Libertyville, IL (US) 60048; Robert E. Haraden, 992 Chesapeake Blvd., Grayslake, IL (US) 60030

( * ) Notice: Subject to any disclaimer, the term of this patent is extended or adjusted under 35 U.S.C. 154(b) by 9 days.

(21) Appl. No.: 10/238,295

(22) Filed: Sep. 10, 2002

(51) Int. Cl.[7] ................................................ A61C 5/04

(52) U.S. Cl. ........................................................ 433/39

(58) Field of Search .............................. 433/39, 40, 47

(56) References Cited

U.S. PATENT DOCUMENTS

| 452,231 A | * | 5/1891 | Meister | 433/161 |
| 5,425,635 A | * | 6/1995 | Croll | 433/39 |

OTHER PUBLICATIONS

B.F. Tofflemire 2,538,486 Reinforcement for a Tooth Filling Jan. 16, 1951 Col. 3, lines 43–55.
Salsarulo 4,303,389 Instrument for the Clinical Application of Fillings for Dental Cavities Dec. 1, 1981 Col. 3, lines 19–30.
Suhonen 5,380,198 Matrix for Dental Medicine and a Device for the Fabrication of Matrix Bands Jan. 10, 1995 Col. 5, lines 16–31.
Nakisher et al. 5,586,883 Gold–Plated Dental Matirx Band Dec. 24, 1996 Col. 2, lines 44–59.
Meyer 5,788,487 Dental Shim Aug. 4, 1998 Col. 3, lines 43–59.

* cited by examiner

*Primary Examiner*—Todd E. Manahan
(74) *Attorney, Agent, or Firm*—Mathew R. P. Perrone, Jr.

(57) ABSTRACT

A matrix band with a coating thereon reduces capillary action between a tooth and the matrix band, while at least one aperture in the matrix band assists with removal of the matrix band from the tooth, after the filling is complete.

13 Claims, 2 Drawing Sheets

MATRIX BAND FOR USE IN DENTISTRY

This invention relates to a matrix band for use by a dentist to provide a framework for applying cavity filling material to a tooth, which minimizes capillary action which causes at least one body fluid to flow into the area between the matrix band and the tooth being filled and does not adhere to the cavity filling material.

BACKGROUND OF THE INVENTION

A matrix band is a common tool used in dentistry. Typically, the matrix band is a thin, flexible piece of material. Generally speaking, the matrix band is metallic in nature. A dentist will position the band around a tooth to be filled. The band is then tightened around the tooth, with a clamping device, in order to form a mold or an appropriate support for applying a filling material to the tooth.

The matrix band of the prior art is metallic, comprising stainless steel. The matrix band must be substantially impervious to, or not reactive with, fluids in a person's mouth. The matrix band must also be made of a metal that is nontoxic. Because the use of a dental matrix band is well defined in U.S. Pat. No. 5,586,883 to Nakisher and Uditsky, incorporated herein by reference, the use thereof need not be further defined.

Although the matrix band is a common and long-used dental implement, problems do exist with the currently used technology. Firstly, capillary action between the matrix band and the tooth causes at least one body fluid, to dampen or contaminate the surface of the tooth being filled. This is extremely undesirable since the presence of an undesirable fluid in the area and sulcular interferes with the adhesion of the cavity filling material to the tooth.

Typically, body fluids do interfere with this work. Such body fluids include, but are not limited to, blood and saliva. Interference is caused, because the best adherence of a filling to a tooth occurs when the tooth is dry.

Another difficulty with a matrix band of the prior art is the tendency of the bands to adhere to the cavity filling material. This adherence may make the matrix band difficult to remove from the tooth when the filing process in complete and may require the dentist to exert extra force on the patient's mouth to remove it. A difficult removal of the matrix band may well be uncomfortable for the patient, and weaken the bond between the cavity filling material and the tooth. Without a good bonding between filling material and the tooth, the dental procedure is ineffective.

Still another difficulty of currently utilized matrix bands is the flat surface of the bands, which contain no indentations where a dental instrument can be used to grasp the band to assist in removing the band after the cavity has been filled. This makes the removal of the band more difficult.

Many devices are known the prior art, which allegedly ease removal of the matrix band from the tooth. One attempt to solve the problem included making the matrix band with a gold plating. However, this matrix band does not solve the capillary action, which causes an undesired body fluid flow into the desired work area.

Use of a polymer coating on the matrix band causes a similar problem. Attempts to use polytetrafluoroethylene, polypropylene, or other synthetic resin coatings are known to be ineffective. None of those coatings prevent fluid from reaching the area of the filling.

While it is not desired to be bound by any particular, the capillary action is believed to occur because the solid gold or gold alloy matrix band, as well as the gold-plated matrix band is not soft enough to seal the tooth or otherwise eliminate capillary action. By the same token, it is felt that the polymer coatings have the same problem.

SUMMARY OF THE INVENTION

Among the many objectives of this invention is the provision of a coated matrix band with a suitable alloy, which minimizes capillary action between the matrix band and the tooth, by creating a seal which keeps the surface of the tooth dry during the filling process.

Another objective of this invention is the provision of a matrix band of the required strength to provide a framework for the cavity filling material.

A further objective of this of this invention is the provision of a matrix band with at least one aperture on the band to assist in the removal of the bands from the tooth when the filling procedure is completed.

Yet another objective of this invention is the provision of a matrix band, which is nontoxic to the patient.

These and other objectives of the invention (which other objectives become clear by consideration of the specification, claims and drawings as a whole) are met by providing a matrix band with a coating thereon, which reduces capillary action between a tooth and the matrix band, while at least one aperture in the matrix band assists with removal of the matrix band from the tooth.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

With the matrix band of this invention being suitable for use in dental procedures and having a coated or a laminated surface thereon, capillary action between the tooth and the band is at least substantially reduced, if not eliminated.

On the ductile matrix band, is applied a metal alloy as either a laminate or a coating. Coating is preferred, because the thickness thereof is more easily controlled. Coatings, with a thickness of about 0.01 millimeter to about 0.2 millimeter, are adequate to reduce the capillary action. Coating with a thickness of about 0.02 millimeter to about 0.1 millimeter reduce the capillary action more effectively. Coating with a thickness of about 0.0025 millimeters (0.0001 inch) to about 0.15 millimeters (0.005 inch) is most effective in reducing, if not eliminating the capillary action.

The desired coating contains tin in a percentage that may vary from 0.1 percent to 100 percent by weight of the coating. Also, operable are coatings having 0.1 percent to 99 percent by weight of tin. The main requirement of the matrix band and any coating thereon is that it be pharmaceutically acceptable or safe to use, especially in dental applications.

Other metals which may be used to make up the remaining percentage of the alloy include: lead, silver, gold, zinc, copper, bismuth, indium, mercury, aluminum, platinum, and combinations thereof. Because of health concerns, the usage of lead and mercury must be limited to a small percentage of the alloy; if they can be used at all. Customarily, the base material for the matrix band is stainless steel.

If desired, at least one aperture may be put in the matrix band. Such an aperture; situated in the central portion of a long edge of the matrix band, with the clamp between the aperture and the tooth, around which the matrix band is placed; is used to assist with the removal of the band from the tooth. This can be accomplished with the standard dental tool commonly known as the explorer.

Figure 1:
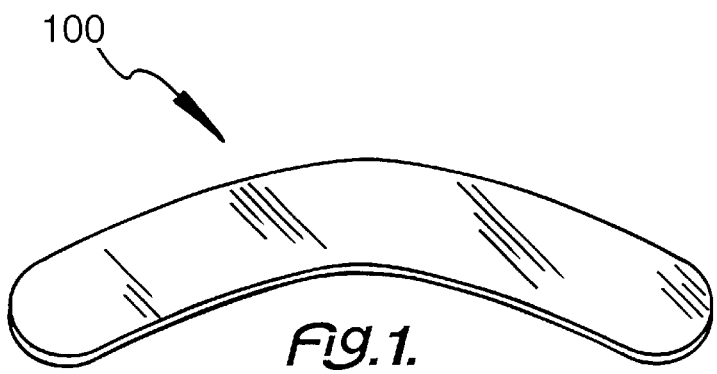
FIG. 1 depicts a perspective view of the coated matrix band 100 of this invention.
Figure 2:
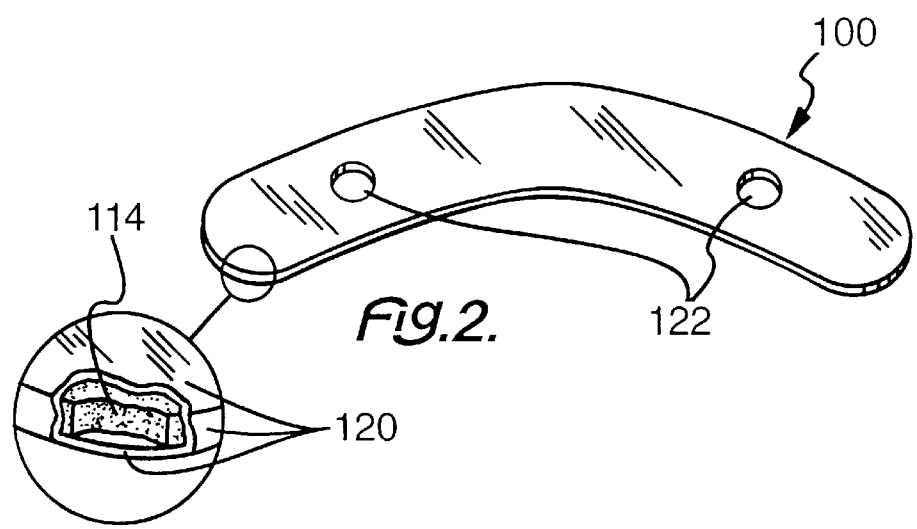
FIG. 2 depicts a perspective view of the coated matrix band 100 of this invention, with aperture 122 therein.

Referring now to FIG. 1 and FIG. 2, the coated matrix band 100 has a support base 114 with a coating 120 applied thereto. The coating 120 may be applied by electroplating or chemical plating, melting the coating materials with appropriate fluxes applied thereto, or otherwise applied thereto.

Figure 3:
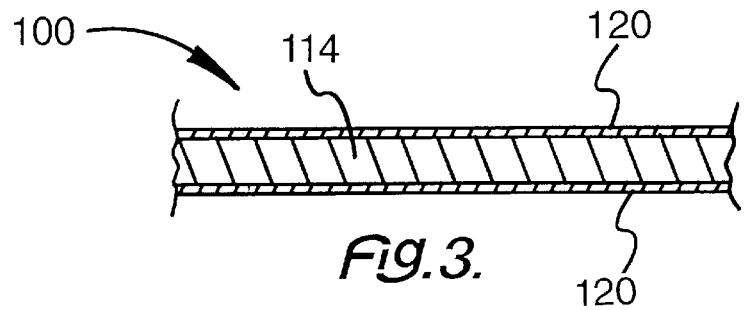
FIG. 3 depicts a side cross-sectioned view of coated matrix band 100 of this invention.

Adding FIG. 3 to the consideration, the thickness of coating 120 on support base 114 is depicted. Thus, a relatively thin coating may provide the necessary release qualities for the coated matrix band 100 from the tooth, while providing reduced capillary action between coated matrix band 100 and the tooth 110.

Figure 4:
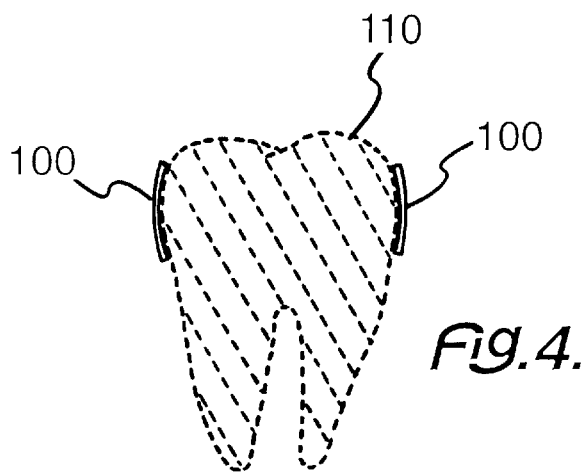
FIG. 4 depicts a side cross-sectioned view of coated matrix band 100 of this invention around tooth 110.
Figure 5:
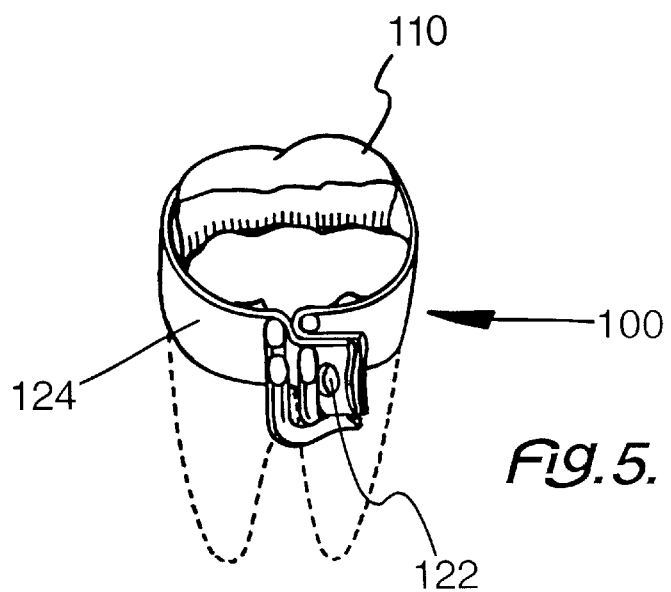
FIG. 5 depicts a perspective view of coated matrix band 100 of this invention around tooth 110.

Adding FIG. 4 and FIG. 5 to the consideration, if desired at least one aperture 122, and preferably two apertures 122 may be centrally located in the width area 124 of coated matrix band 100. Aperture 122 has no or minimal effect on the desired reduced capillary action, and permits the use of a dental instrument, such as an explorer (not shown) to assist in the removal of coated matrix band 100.

In the following examples, which are intended to illustrate without unduly limiting the invention disclosed herein, all parts and percentages are by weight, unless otherwise specified.

EXAMPLE ONE

With the coated matrix band 100; having a coating 120 on a stainless steel support base 114, the coating 120 being based on a tin alloy of two percent by weight gold and 98 percent by weight tin; being applied to a tooth under repair, fluid running into the area of the tooth under repair is greatly reduced.

EXAMPLE TWO

The procedure of Example One is repeated except that the tin alloy is replaced with an alloy of two percent by weight tin and 98 percent by weight indium. Similar results to those of Example One are obtained.

EXAMPLE THREE

The procedure of Example One is repeated except that the tin alloy is replaced with an alloy of two percent by weight gold and 98 percent by weight indium. Similar results to those of Example One are obtained.

EXAMPLE FOUR

The procedure of Example One is repeated except that the tin alloy is replaced with an alloy mixture of equal parts by weight of two percent by weight gold and 98 percent by weight tin and two percent by weight tin and 98 percent by weight indium. Similar results to those of Example One are obtained.

EXAMPLE FIVE

With the prior art matrix band 100 of stainless steel applied to a tooth under repair, fluid running into the area of the tooth under repair is sufficient to destroy a quality filling with good bond strength.

EXAMPLE SIX

With the matrix band having a polytetrafluoroethylene coating thereon applied to a tooth under repair, fluid running into the area of the tooth under repair has results similar to Example 5. The polytetrafluoroethylene coating delaminates or scrapes off of the matrix band, resulting in a poor quality filling.

EXAMPLE SEVEN

The procedure of Example Six is repeated except that the polytetrafluoroethylene is replaced with polypropylene. Similar results to those Example Six are obtained.

EXAMPLE EIGHT

The procedure of Example 1 is repeated, except for two diametrically opposed apertures 122 are present in the matrix band 100. A common dental tool known as the explorer, fits in aperture 122 and facilitates removal of the matrix band, with no significant increase in capillary action.

This application; taken as a whole with the abstract, specification, claims, and drawings being combined; provides sufficient information for a person having ordinary skill in the art to practice the invention as disclosed and claimed herein. Any measures necessary to practice this invention are well within the skill of a person having ordinary skill in this art after that person has made a careful study of this disclosure.

Because of this disclosure and solely because of this disclosure, modification of this method and device can become clear to a person having ordinary skill in this particular art. Such modifications are clearly covered by this disclosure.

What is claimed and sought to be protected by Letters Patent of the United States is:

1. In a matrix band for use in dentistry, the improvement comprising a coating on the matrix band, which minimizes capillary action between the matrix band and a tooth being filled while the matrix band is positioned therearound in order to support adherence of a filling material to the tooth, the matrix band further comprising:
   (a) the coating being a metal;
   (b) the coating containing tin in a percentage from 0.1 percent to 100 percent by weight;
   (c) the coating having a thickness of about 0.01 millimeter to about 0.2 millimeter; and
   (d) the coating providing a reduction of body fluid flow into the area between the matrix band and the tooth being filled.

2. The matrix band of claim 1 further comprising:
   (a) the coating having a thickness of about 0.02 millimeter to about 0.1 millimeter; and
   (b) the matrix band having at least one aperture in order to assist with a removal procedure of the matrix band from the tooth.

3. The matrix band of claim 2 further comprising:
   (a) the coating having a thickness of about 0.0025 millimeter to about 0.15 millimeter; and
   (b) the matrix band being ductile.

4. The matrix band of claim 3 further comprising:
(a) the coating being a metal alloy; and
(b) the metal alloy containing tin in a percentage from 0.1 percent to 99 percent by weight.

5. The matrix band of claim 4 further comprising:
(a) the alloy comprising tin; and at least one metal selected from the group consisting of lead, silver, gold, zinc, copper, bismuth, indium, mercury, aluminum and platinum; and
(b) the alloy being pharmaceutically acceptable.

6. The matrix band of claim 5 further comprising:
(a) the matrix band having a clamp for securing the matrix band around the tooth;
(b) the clamp being between the tooth and the at least one aperture; and
(c) the at least one aperture being adapted to assist with a removal of the matrix band from the tooth.

7. A coated matrix band for use in dentistry comprising:
(a) a support base and a coating on the support base forming the coated matrix band;
(b) the coating minimizing a capillary action between the coated matrix band and a tooth being filled while the matrix band is positioned therearound in order to support adherence of a filling material to the tooth;
(c) the coating having a thickness of about 0.01 millimeter to about 0.2 millimeter;
(d) the coating providing a reduction of body fluid flow into the area between the matrix band and the tooth being filled;
(e) the coating being a metal; and
(f) the coating containing tin in a percentage from 0.1 percent to 100 percent by weight.

8. The coated matrix band of claim 7 further comprising:
(a) the coating having a thickness of about 0.02 millimeter to about 0.1 millimeter; and
(b) the matrix band having at least one aperture in order to assist with a removal procedure of the matrix band from the tooth.

9. The coated matrix band of claim 8 further comprising:
(a) the coating having a thickness of about 0.0025 millimeter to about 0.15 millimeter; and
(b) the matrix band being ductile.

10. The coated matrix band of claim 9 further comprising:
(a) the coating being a metal alloy; and
(b) the metal alloy containing tin in a percentage from 0.1 percent to 99 percent by weight.

11. The coated matrix band of claim 10 further comprising:
(a) the alloy comprising tin; and at least one metal selected from the group consisting of lead, silver, gold, zinc, copper, bismuth, indium, mercury, aluminum and platinum; and
(b) the alloy being pharmaceutically acceptable.

12. The coated matrix band of claim 11 further comprising:
(a) the matrix band having a clamp securing the matrix band around the tooth;
(b) the clamp being between the tooth and the at least one aperture; and
(c) the at least one aperture being adapted to assist with a removal of the matrix band from the tooth.

13. The matrix band of claim 12 further comprising the alloy for the coating of the matrix band being at least one pharmaceutically acceptable alloy selected from the group consisting of a first alloy having about two percent by weight gold and about 98 percent by weight tin, a second alloy having about two percent by weight tin and 98 percent by weight indium, a third alloy having about two percent by weight gold and about 98 percent by weight indium, a fourth alloy having about two percent by weight tin and about 98 percent by weight indium.

* * * * *